US011676729B2

(12) United States Patent
Wen et al.

(10) Patent No.: US 11,676,729 B2
(45) Date of Patent: Jun. 13, 2023

(54) MONITORING METHOD, MONITORING DEVICE AND MONITORING SERVER

(71) Applicant: BOE TECHNOLOGY GROUP CO., LTD., Beijing (CN)

(72) Inventors: Ken Wen, Beijing (CN); Wenchu Dong, Beijing (CN); Honglei Zhang, Beijing (CN); Siyu Zhu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 428 days.

(21) Appl. No.: 16/911,387

(22) Filed: Jun. 24, 2020

(65) Prior Publication Data

US 2020/0411197 A1 Dec. 31, 2020

(30) Foreign Application Priority Data

Jun. 27, 2019 (CN) .......................... 201910569138.6

(51) Int. Cl.
| G16H 50/30 | (2018.01) |
| G16H 30/20 | (2018.01) |
| G16H 10/60 | (2018.01) |
| H04W 4/80 | (2018.01) |
| A61B 5/02 | (2006.01) |
| A61B 5/145 | (2006.01) |
| A61B 5/00 | (2006.01) |

(52) U.S. Cl.
CPC ........... *G16H 50/30* (2018.01); *A61B 5/0022* (2013.01); *A61B 5/02* (2013.01); *A61B 5/145* (2013.01); *G16H 10/60* (2018.01); *G16H 30/20* (2018.01); *H04W 4/80* (2018.02)

(58) Field of Classification Search
None
See application file for complete search history.

(56) References Cited

U.S. PATENT DOCUMENTS

| 10,172,517 | B2 | 1/2019 | Jain et al. |
| 10,624,550 | B2 * | 4/2020 | Soli ................... A61B 5/02438 |
| 2015/0137997 | A1 * | 5/2015 | Huang ................. A61B 5/1112 |
| | | | 340/870.07 |
| 2017/0245759 | A1 | 8/2017 | Jain et al. |

FOREIGN PATENT DOCUMENTS

| CN | 201379558 Y | 1/2010 |
| CN | 104055487 A | 9/2014 |

(Continued)

OTHER PUBLICATIONS

Office Action issued in corresponding Chinese Patent Application No. 201910569138.6, dated Aug. 11, 2022.

*Primary Examiner* — Kristy A Haupt
(74) *Attorney, Agent, or Firm* — McDermott Will & Emery LLP

(57) ABSTRACT

The present disclosure provides a monitoring method, a monitoring device and a monitoring server. The monitoring method includes: acquiring physical sign information of a user; determining whether a physical sign of the user is in an abnormal state based on the physical sign information; acquiring first physical symptom information of the user in response to the physical sign of the user being in the abnormal state; and transmitting the physical sign information and the first physical symptom information to a monitoring server to determine a health status of the user.

17 Claims, 5 Drawing Sheets

(56) References Cited

FOREIGN PATENT DOCUMENTS

| | | | |
|---|---|---|---|
| CN | 104382570 | A | 3/2015 |
| CN | 105046873 | A | 11/2015 |
| CN | 105141743 | A | 12/2015 |
| CN | 105769143 | A | 7/2016 |
| CN | 107169265 | A | 9/2017 |
| CN | 108778097 | A | 11/2018 |

\* cited by examiner

MONITORING METHOD, MONITORING DEVICE AND MONITORING SERVER

CROSS-REFERENCE TO RELATED APPLICATION(S)

This application claims priority to the Chinese Patent Application No. 201910569138.6, filed on Jun. 27, 2019, which is incorporated herein by reference in its entirety.

TECHNICAL FIELD

The present disclosure relates to the medical field, and more particularly, to a monitoring method, a monitoring device, and a monitoring server.

BACKGROUND

Generally, a health monitoring apparatus may monitor a physical sign of a user in real time through a monitoring device. When an emergency occurs or abnormal physical sign information is detected, a geographic location of the user and the abnormal physical sign information are transmitted to a monitoring center, a doctor, or a family member, so as to take certain rescue measures. However, the user information which may be known by the monitoring center or related personnel is not comprehensive, and thereby a health status of the user may not be accurately determined.

SUMMARY

The embodiments of the present disclosure provide a monitoring method, comprising:
acquiring physical sign information of a user;
determining whether a physical sign of the user is in an abnormal state based on the physical sign information;
acquiring first physical symptom information of the user in response to the physical sign of the user being in the abnormal state; and
transmitting the physical sign information and the first physical symptom information to a monitoring server to determine a health status of the user.

In some embodiments, acquiring first physical symptom information of the user comprises:
transmitting, to a first electronic device with which a short-range communication connection has been established based on a short-range communication protocol, a first request for requesting the first electronic device to acquire the first physical symptom information of the user; and
receiving the first physical symptom information transmitted by the first electronic device.

In some embodiments, the monitoring method further comprises:
acquiring location information of the user; and
transmitting the location information to the monitoring server, so that the monitoring server acquires second physical symptom information of the user based on the location information.

In some embodiments, acquiring second physical symptom information of the user based on the location information comprises:
transmitting, to a second electronic device within a first preset range from the user based on the location information, a second request for requesting the second electronic device to acquire the second physical symptom information of the user; and
receiving the second physical symptom information transmitted by the second electronic device.

In some embodiments, acquiring second physical symptom information of the user based on the location information comprises:
transmitting, to a traffic server, a third request comprising the location information for requesting the traffic server to control a traffic image collector within a second preset range from the user to acquire the second physical symptom information of the user; and
receiving the second physical symptom information transmitted by the traffic server.

In some embodiments, the traffic image collector comprises at least one of a camera installed on a street or a driving recorder installed on a vehicle.

In some embodiments, the monitoring method further comprises:
determining, by the monitoring server, a medical server at the shortest distance from the user based on the location information; and
transmitting, by the monitoring server, help information comprising at least one of the physical sign information, the location information, the first physical symptom information, or the second physical symptom information to the medical server.

In some embodiments, the monitoring method further comprises:
acquiring medical record information of the user in response to the physical sign of the user being in the abnormal state;
analyzing a cause of occurrence of the abnormal state based on the physical sign information and the medical record information of the user; and
transmitting an analysis result to the monitoring server.

In some embodiments, the physical sign information comprises at least one of a blood pressure, a blood glucose, a blood oxygen content, a heart rate, or a pulse.

The embodiments of the present disclosure further provide a monitoring device, comprising:
a memory having stored therein instructions; and
a processor configured to execute the instructions to:
acquire physical sign information of a user;
determine whether a physical sign of the user is in an abnormal state based on the physical sign information;
acquire first physical symptom information of the user in response to the physical sign of the user being in the abnormal state; and
transmit the physical sign information and the first physical symptom information to a monitoring server to determine a health status of the user.

In some embodiments, the monitoring device further comprises:
a plurality of sensors coupled to the processor, and configured to collect the physical sign information of the user and provide the physical sign information to the processor.

In some embodiments, the processor is further configured to transmit, to a first electronic device with which a short-range communication connection has been established based on a short-range communication protocol, a first request for requesting the first electronic device to acquire the physical symptom information of the user, and receive the physical symptom information transmitted by the first electronic device.

In some embodiments, the monitoring device further comprises a first communication interface through which the processor communicates with the first electronic device.

In some embodiments, the monitoring device further comprises:

a locator coupled to the processor, and configured to acquire location information of the user and provide the location information to the processor, wherein the processor is further configured to transmit the location information to the monitoring server, so that the monitoring server acquires physical symptom information of the user based on the location information.

In some embodiments, the processor is further configured to:

acquire medical record information of the user in response to the physical sign of the user being in the abnormal state;

analyze a cause of occurrence of the abnormal state based on the physical sign information and the medical record information of the user; and transmit an analysis result to the monitoring server.

In some embodiments, the monitoring device further comprises a second communication interface through which the processor communicates with the monitoring server.

The embodiments of the present disclosure further provide a monitoring server comprising a memory and a processor, wherein the memory has stored therein instructions, and the processor is configured to execute the instructions to:

receive physical sign information and first physical symptom information of a user from a monitoring device, wherein the first physical symptom information is acquired by the monitoring device in response to a physical sign of the user being in an abnormal state; and determine a health status of the user according to the physical sign information and the first physical symptom information.

In some embodiments, the processor is further configured to:

receive location information of the user from the monitoring device;

transmit, to a second electronic device within a first preset range from the user, a second request for requesting the second electronic device to acquire second physical symptom information of the user; and receive the second physical symptom information transmitted by the second electronic device.

In some embodiments, the processor is further configured to:

transmit, to a traffic server, a third request comprising the location information for requesting the traffic server to control a traffic image collector within a second preset range from the user to collect the second physical symptom information of the user based on the location information; and receive the second physical symptom information transmitted by the traffic server.

In some embodiments, the processor is further configured to:

determine a medical server at the shortest distance from the user based on the location information; and transmit help information comprising at least one of the physical sign information, the location information, the first physical symptom information, or the second physical symptom information to the medical server.

BRIEF DESCRIPTION OF THE ACCOMPANYING DRAWINGS

In order to more clearly explain the technical solutions according to the embodiments of the present disclosure; the accompanying drawings of the embodiments will be briefly described below. Obviously, the accompanying drawings in the following description only relate to some embodiments of the present disclosure, rather than limit the present disclosure.

DETAILED DESCRIPTION

In order to make the purposes, technical solutions and advantages of the embodiments of the present disclosure more clear, the technical solutions according to the embodiments of the present disclosure will be described clearly and completely in conjunction with the accompanying drawings of the embodiments of the present disclosure. Obviously, the described embodiments are a part of the embodiments of the present disclosure, but not all the embodiments. All other embodiments obtained by those of ordinary skill in the art based on the described embodiments of the present disclosure without any creative work fall within the protection scope of the present disclosure.

Unless otherwise defined, the technical terms or scientific terms used in the present disclosure should have the usual meanings understood by those skilled in the art to which the present disclosure belongs. Similar words such as "comprise" or "include" mean that an element or item appearing before the word cover elements or items listed after the word and their equivalents, but do not exclude other elements or items. "Connected with" or "connected to" and similar words are not limited to physical or mechanical connections, but may include electrical connections, whether direct or indirect. "Up", "down", "left", "right", etc. are only used to indicate a relative positional relationship. After absolute positions of objects described change, the relative positional relationship may also change accordingly.

In order to keep the following descriptions of the embodiments of the present disclosure clear and concise, detailed descriptions of known functions and known components are omitted in the present disclosure.

Figure 1:
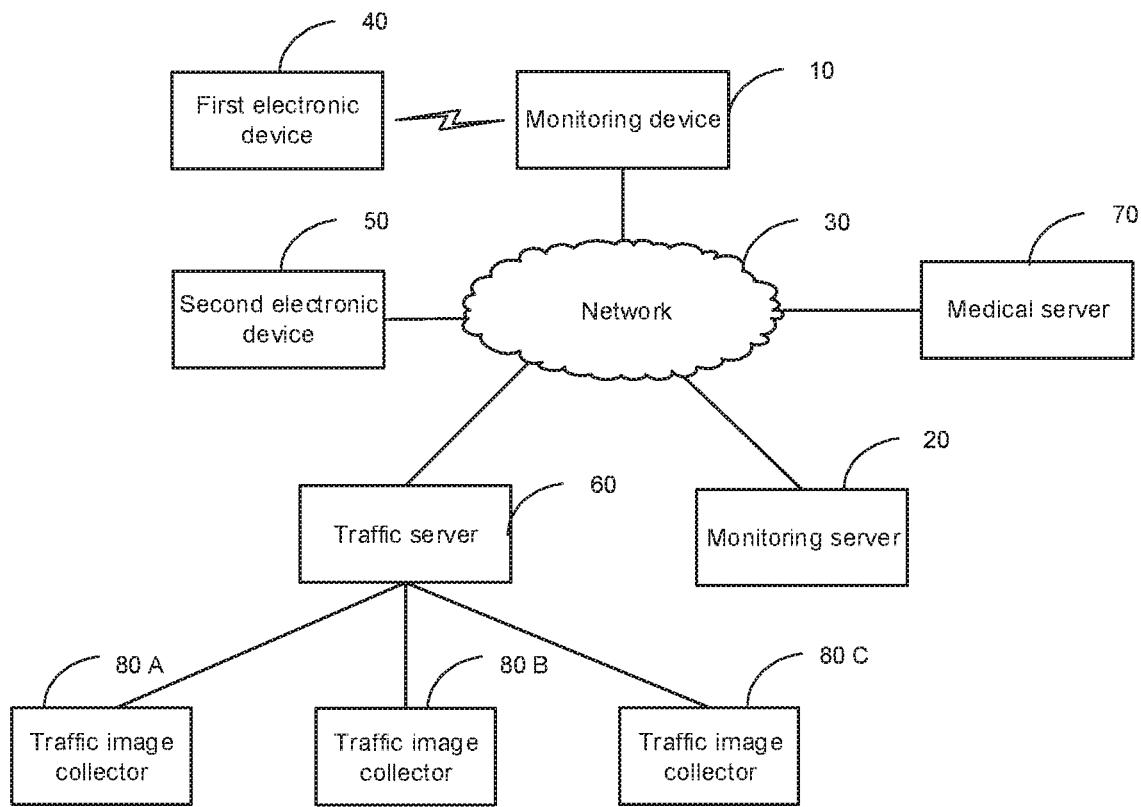
FIG. 1 is a schematic diagram of an application environment of a monitoring method according to an embodiment of the present disclosure.

FIG. 1 is a schematic diagram of an application environment of a monitoring method according to an embodiment of the present disclosure. The environment shown in FIG. 1 comprises a monitoring device 10 and a monitoring server 20, and the monitoring device 10 and the monitoring server 20 may be communicatively coupled through a network 30. A short-range communication connection has been established between a first electronic device 40 and the monitoring device 10. The monitoring server 20 is also communicatively coupled to a second electronic device 50, a traffic server 60, and a medical server 70 through the network 30. The traffic server 60 is coupled to a plurality of traffic image collectors 60A, 60B, and 60C in a wired or wireless manner, for example.

The monitoring device 10 may be implemented as various devices having an ability to monitor a physical sign of a user, for example, but not limited to, a bracelet, a head-mounted or arm-mounted monitoring device, or a smart phone etc. The monitoring server 20 may be located in a medical monitoring institution, and uses various monitoring information provided by the monitoring device 10 to provide health monitoring services to the user. Examples of the network 30 comprise, but not limited to, the Internet, a local area network, etc. The first electronic device 30 may be an electronic device which has established a short-range communication connection such as a Bluetooth connection with the monitoring device 10. For example, the electronic device 30 may be a mobile phone carried by the user, wherein the mobile phone has established a Bluetooth connection with the monitoring device 10 carried by the user. There may be a plurality of traffic servers 60, which are distributed in different geographical locations. Each of the traffic servers 60 may be coupled to a plurality of traffic image collectors 80A, 80B, and 80C. Examples of the traffic image collectors 80A, 80B, and 800 comprise, but not limited to, cameras installed on streets or driving recorders installed on vehicles. There may be one or more medical servers 70, which may be located in a medical service institution or a hospital.

Figure 2:
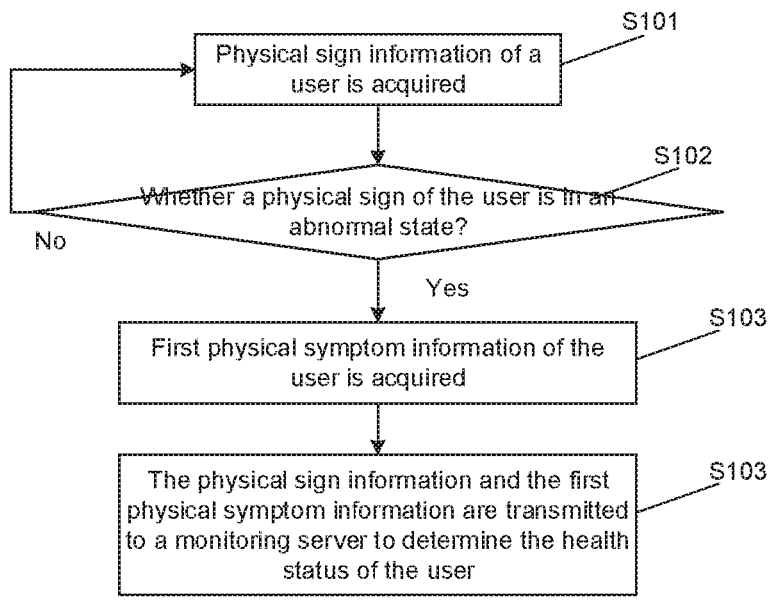
FIG. 2 is a flowchart of a monitoring method according to an embodiment of the present disclosure.

FIG. 2 is a flowchart of a monitoring method according to an embodiment of the present disclosure. As shown in FIG. 2, the present disclosure provides a monitoring method, which comprises steps S101 to S104.

In step S101, physical sign information of a user is acquired. The physical sign information may comprise a variety of physiological information which may characterize a health status of the user, for example, a heart rate, a blood oxygen content, a blood pressure, a blood sugar, etc. The physical sign information may be acquired through various monitoring devices, for example, a monitoring bracelet, a head-mounted or arm-mounted monitoring device or a smart phone, etc., which is not specifically limited here.

In step S102, it is determined whether a physical sign of the user is in an abnormal state based on the physical sign information, and if so, step S103 is executed; otherwise; the procedure returns to step S101. The physical sign information comprises a series of data which characterize the health status of the user, for example, a heart rate, a pulse, a blood pressure, respiration, blood oxygen, etc. In some embodiments, the physical sign information which is acquired currently may be determined according to pre-stored physical sign information of a healthy person in a normal physiological state. For example, if a normal range of a heart rate of the healthy person in the normal physiological state is 60-100 beats/min, and a heart rate which is acquired currently is 120 beats/min, it may be determined that the current heart rate is in an abnormal state. In some embodiments, the user's own physical sign information in the normal physiological state which is determined according to stored user's own historical physical sign information may also be used to make determination on the physical sign information which is acquired currently. For example, if a normal range of the heart rate of the user in the normal physiological state is determined to be 60-90 beats/min according to the historical physical sign information of the user, and the heart rate which is acquired currently is 95 beats/min, it may be determined that the current heart rate of the user is in an abnormal state. In this way, more accurate determination may be made on the health status of the user, which is more personalized.

In step S103, first physical symptom information of the user is acquired.

In the exemplary environment of FIG. 1, the first physical symptom information may be acquired by the monitoring device 10 or may also be acquired by the first electronic device 40 which is requested by the monitoring device 10 to establish short-range communication therewith, which will be described in further detail below. The first physical symptom information may be the external manifestation of the user, for example, looks, body movements such as convulsions, vomiting etc., sounds, etc.

In step S104, the physical sign information and the first physical symptom information are transmitted to a monitoring server (hereinafter also referred to as a first information receiving terminal) to determine the health status of the user.

For example, in a case where the physical sign information is in an abnormal state, the monitoring device 10 acquires the first physical symptom information of the user, and transmits first information based on the physical sign information and the first physical symptom information, so that the first information receiving terminal determines the health status of the user according to the physical sign information and the physical symptom information.

When medical care workers make determination on the current health status of the user, the medical care workers may more accurately determine the current health status of the user based on the physical sign information in combination with the external physical symptom information, and may improve work efficiency, so as to avoid missing the best time for treatment of the user, thereby improving the efficiency of treatment for the user.

In some embodiments, the first information may further comprise location information, help content, and a preliminary processing result of the physical sign information etc. For example, pre-processing and feature extraction are performed on electrocardiosignal data to obtain a result that an ST segment of the electrocardiosignal physical signal raises, and this result is transmitted to medical care workers to help the medical care workers quickly determine the health status of the user and take relevant rescue measures in advance, thereby improving the efficiency of treatment.

In some embodiments, the physical symptom information (comprising the first physical symptom information and second physical symptom information) may be obtained from an image or video related to the user, and the image or video related to the user may be obtained by the monitoring device which acquires the physical sign information. For example, the monitoring device comprises a camera apparatus. In a case where the physical sign information is in an abnormal state, the camera apparatus is turned on by the monitoring device to acquire the physical symptom information of the user. As another example, although the monitoring device does not comprise a camera apparatus, the monitoring device may acquire the physical symptom information through interaction with other external devices. In some embodiments, if the first information transmitted does not carry physical symptom information, the physical symptom information may also be obtained by the first information receiving terminal. For example, after receiving the first information transmitted based on the physical sign information, the first information receiving terminal transmits a first request (hereinafter also referred to as a second control command) to a first electronic device (hereinafter also referred to as a first device) which establishes a connection with the monitoring device which acquires the physical sign information, so that, after receiving the second control command, the first device turns on a camera apparatus thereon, acquires physical symptom information of the user using photos or videos taken by the camera apparatus, and transmits the acquired physical symptom information of the user to the first information receiving terminal.

In some embodiments, the first information comprises location information of the user, and after receiving the first information which is transmitted based on the physical sign information, the first information receiving terminal transmits, based on the location information, a second request to a second electronic device (hereinafter also referred to as a second device) within a preset range from a location indicated by the location information. After receiving the second request, the second device may ask a user thereof whether to help acquire physical symptom information of the user corresponding to the location information, and after the user confirms to help acquire the physical symptom information of the user, a camera apparatus of the second device is turned on to acquire the physical symptom information of the user, and transmits the physical symptom information to the first information receiving terminal. In some embodiments, after the first information receiving terminal receives the first information which is transmitted based on the physical sign information, the first information receiving terminal transmits a third request to a traffic server based on the location information. The traffic server may be a traffic server which is determined based on the location information to be close to (for example, within a first preset range from or closest to) the user. In some embodiments, the traffic server may be a server of a vehicle monitoring system, which receives images and/or videos transmitted by various camera apparatuses for monitoring vehicles, and after receiving the third request, the traffic server determines camera apparatuses within a second preset range from (or closest to) the location of the user according to the location information, receives images or videos acquired by the camera apparatuses which may characterize physical symptoms of the user, and transmits the images or the videos to the first information receiving terminal, so as to facilitate medical care workers to make accurate determination on the current health status of the user according to the first information received by the first information receiving terminal in combination with the physical symptom information, so as to avoid missing the best time for treatment of the user, thereby improving the efficiency of treatment of the user.

In some embodiments, the first information may be transmitted by the monitoring device which acquires the physical sign information of the user, or may also be transmitted by other devices which establish a communication connection with the monitoring device, which is not specifically limited herein. The first information receiving terminal may be a server of a monitoring center, other devices associated with identification information of the user, etc. In some embodiments, the first information receiving terminal may also be a device which is determined according to the location information of the user to be within a certain range from the user. For example, the monitoring device may use a Bluetooth Low Energy (BLE) communication module to transmit the first information to an electronic device within a range of 50 meters from the user in a broadcast manner.

With the monitoring method according to the embodiments of the present disclosure, it may be determined whether the user is currently in an abnormal state according to the acquired physical sign information, and the first information is transmitted in a case where the user is currently in the abnormal state, wherein the first information may comprise the physical sign information or a combination of the physical sign information and the physical symptom information. When the first information receiving terminal receives the first information, the first information receiving terminal may make a response, so that the medical care workers may accurately determine the current health status of the user directly or indirectly according to the first information, so as to avoid missing the best time for treatment of the user, thereby improving the efficiency of treatment of the user.

In some embodiments, acquiring the physical symptom information of the user may comprise: transmitting, to the first device which has established a connection, a first request (hereinafter also referred to as a second control command) for requesting the first device to acquire the physical symptom information; and receiving the physical symptom information transmitted by the first device. For example, the monitoring device used to acquire the physical sign information of the user may establish a connection with the first device in a wired or wireless manner. For example, in one embodiment, the monitoring device is a monitoring bracelet, and the first device is a smart phone which has established a Bluetooth connection with the monitoring bracelet. After receiving the second control command transmitted by the monitoring device, the first device turns on a camera apparatus thereon, and uses photos or videos taken by the camera apparatus to acquire the physical symptom information of the user. The first device transmits the acquired physical symptom information of the user to the monitoring device, so that the monitoring device transmits the first information based on the physical sign information and the physical symptom information. In some embodiments, in order to save power, the monitoring device may establish a connection with the first device in a case where it is determined that the physical sign information is in an abnormal state.

In some embodiments, acquiring the physical symptom information of the user comprises: acquiring location information of the user; and transmitting second information based on the location information to acquire physical symptom information (second physical symptom information) through the second information. For example, the second information is an operation request (comprising the second request and the third request) for requesting other devices to acquire the physical symptom information of the user, and may carry the location information of the user, help content, and identification information of the monitoring device for acquiring the physical sign information of the user. In some embodiments, the second information (the second request) may be transmitted to the second device within the preset range from the location indicated by the location information. After receiving the second information, the second device may ask a user of the second device whether to help acquire the physical symptom information of the user corresponding to the identification information of the monitoring device, and after the user confirms to help acquire the physical symptom information of the user, the camera apparatus of the second device is turned on to acquire the physical symptom information of the user of the monitoring device. After acquiring the physical symptom information, the second device transmits the physical symptom information to the corresponding monitoring device based on the received identification information of the monitoring device, so that the monitoring device transmits the first information based on the physical sign information and the physical symptom information to improve the efficiency of treatment of the user of the monitoring device.

In some embodiments, transmitting the second information based on the location information to acquire the physical symptom information through the second information comprises: transmitting the second information (the third request) to the traffic server to cause the traffic server to acquire physical symptom information collected by a traffic image collector (hereinafter also referred to as a third device) based on the second information, wherein the second information carries the location information; and receiving the physical symptom information transmitted by the traffic server. The traffic server may be a traffic server which is determined based on the location information to be close to (for example, within the first preset range from or closest to) the user. In some embodiments, the traffic server may be a server of the vehicle monitoring system, which receives images and/or videos transmitted by various camera apparatuses (traffic image collectors) for monitoring vehicles. In a case where the physical sign information is in an abnormal state, the second information may be transmitted to the traffic server based on the location information of the user. After receiving the second information, the traffic server may determine camera apparatuses (traffic image collectors) which are close to (for example, within the second preset range from) the location of the user according to the location information, receive images or videos acquired by the camera apparatuses which may characterize the physical symptom information of the user, and transmit the images or the videos to the monitoring device for monitoring the physical sign information of the user. The monitoring device may process the images to obtain the physical symptom information. The traffic server may also be other servers, for example, an image collection server in a road network.

In some embodiments, transmitting the first information based on the physical sign information and the physical symptom information comprises: determining a medical server (hereinafter also referred to as a fourth device) at the shortest distance to the user based on the location information; and transmitting the first information to the medial server based on the physical sign information and the physical symptom information. The medical server may be various kinds of devices which are determined based on the location information to be at the shortest distance to the user, for example, a server of a monitoring center, a server of a hospital information system, an electronic device which has established a connection with the device which transmits the first information, etc. The first information is transmitted to the medical server at the shortest distance to the user, so that medical care workers in a hospital may rush to the site to treat the user as soon as possible after receiving the first information, thereby improving the efficiency of the treatment of the user.

In some embodiments, the monitoring method further comprises: in a case where the physical sign information is in an abnormal state, analyzing a cause of occurrence of the abnormal state based on the physical sign information and medical record information of the user, for example, determining whether the user satisfies characteristics of a disease recorded in the medical record information of the user based on physical sign information and/or a preliminary processing result of the physical sign information: and generating and transmitting the first information based on an analysis result, so that the medical care workers may quickly and accurately determine the current health status of the user according to the analysis result in combination with the physical sign information and the physical symptom information, thereby improving the efficiency of the treatment of the user.

Figure 3:
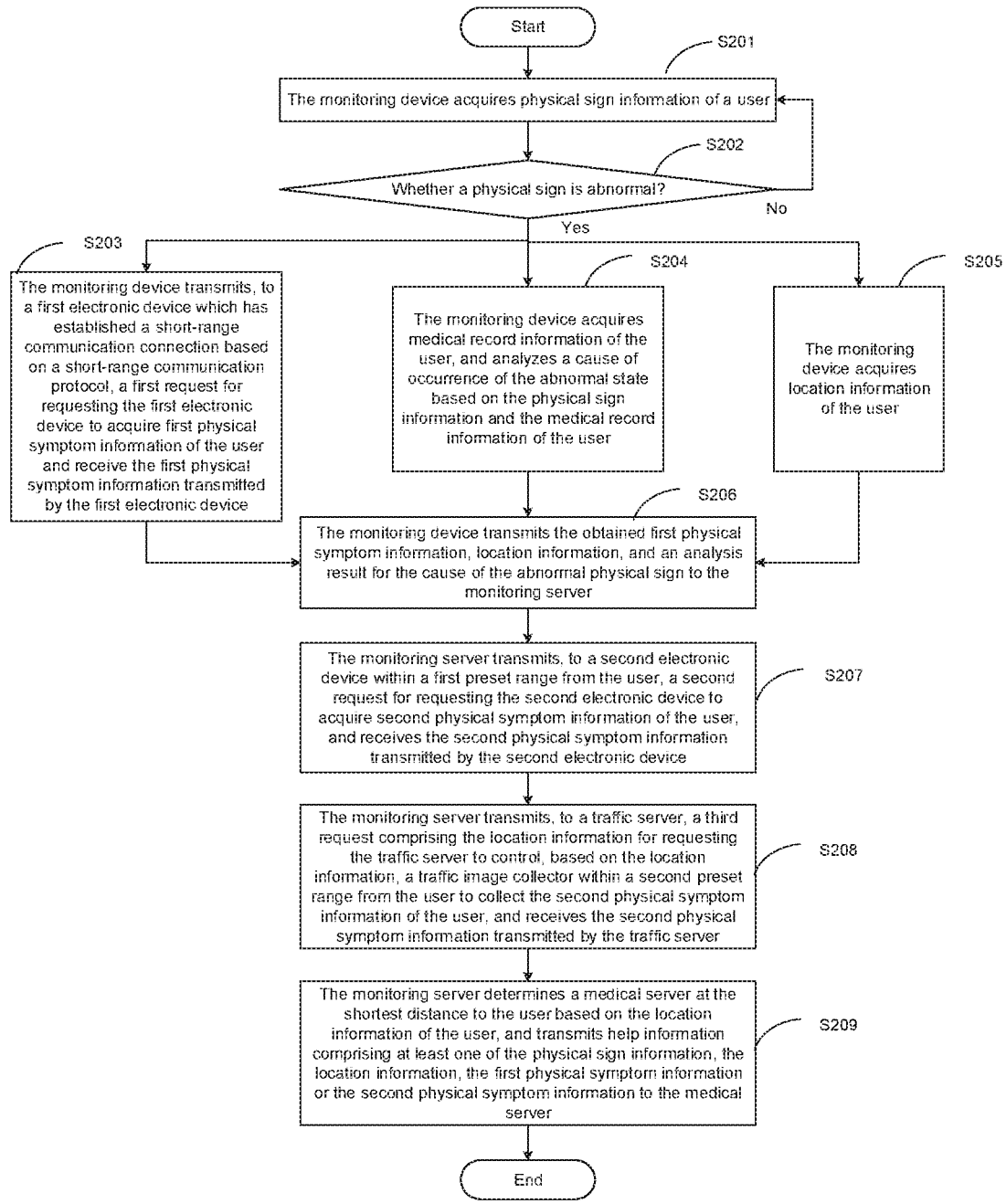
FIG. 3 is a flowchart of a monitoring method according to another embodiment of the present disclosure.

FIG. 3 is a flowchart of a monitoring method according to an embodiment of the present disclosure.

In step S201, the monitoring device acquires physical sign information of a user.

In step S202, the monitoring device determines whether a physical sign of the user is in an abnormal state based on the physical sign information, and if so, steps S203, S204, and S205 are executed; otherwise, the procedure returns to step S201.

In step S203, the monitoring device transmits, to a first electronic device which has established a short-range communication connection based on a short-range communication protocol, a first request for requesting the first electronic device to acquire first physical symptom information of the user and receive the first physical symptom information transmitted by the first electronic device. For example, in the environment shown in FIG. 1, the monitoring device 10 may transmit a first request to the first electronic device 40 which has established a Bluetooth connection with the monitoring device 10 based on a Bluetooth communication protocol. In response to the first request, the first electronic device 40 may acquire, for example, through a collection apparatus such as a camera, a microphone, etc. installed therein, the information of the user such as sounds, images, and videos, which may reflect physical symptoms (for example, an abnormal face, vomiting, convulsions, syncope, etc.) of the user and transmit the information to the monitoring device 10 as first physical symptom information.

In step S204, the monitoring device acquires medical record information of the user, and analyzes a cause of occurrence of the abnormal state based on the physical sign information and the medical record information of the user. For example, in the environment of FIG. 1, the monitoring device 10 may store the medical record information of the user locally, or download the medical record information of the user from other external devices (for example, a medical information server in a hospital which the user previously visited). The monitoring device 10 may analyze a cause of occurrence of, for example, an abnormal heart rate according to the physical sign information and the medical record information of the user. In some embodiments, the monitoring device 10 may transmit the medical record information to the monitoring server 20 in the following step S207 for analysis and processing.

In step S205, the monitoring device acquires location information of the user. For example, the monitoring device may acquire the location information using its own Global Positioning System (GPS) locator.

In step S206, the monitoring device transmits the obtained first physical symptom information, location information, and an analysis result for the cause of the abnormal physical sign to the monitoring server. For example, the monitoring device may include the first physical symptom information, the location information, and the analysis result for the cause of the abnormal physical sign in help information and transmit the help information to the monitoring server. Monitoring personnel who use the monitoring server may determine a health status of the user according to the help information and take corresponding rescue measures.

In step S207, the monitoring server transmits, to a second electronic device within a first preset range from the user, a second request for requesting the second electronic device to acquire second physical symptom information of the user, and receives the second physical symptom information transmitted by the second electronic device. For example, in the environment of FIG. 1, the monitoring server 20 may determine one or more second electronic devices 50 within the first preset range from the user (for example, mobile phones of pedestrians within 100 meters from the user) according to the location information, and transmit, to the one or more second electronic devices 50, a second request for requesting the electronic device(s) 50 to capture voice, videos, or images of the user as the second physical symptom information. After receiving the request, the second electronic device 50 may transmit the second physical symptom information acquired by itself to the monitoring server 20.

In step S208, the monitoring server transmits, to a traffic server, a third request comprising the location information for requesting the traffic server to control, based on the location information, a traffic image collector within a second preset range from the user to collect the second physical symptom information of the user, and receives the second physical symptom information transmitted by the traffic server.

For example, in the environment of FIG. 1, it is assumed that there are a plurality of traffic servers 60. The monitoring server 20 may search for a traffic server 60 closest to the user based on the location information of the user, and transmit the second request to the traffic server 60. The traffic server 60 may control a traffic image collector (for example, the image collector 60B in FIG. 1) within the second preset range from the user based on the location information in the second request to collect the second physical symptom information of the user and provide the second physical symptom information to the traffic server 60. The traffic server 60 may transmit the received second physical symptom information to the monitoring server 20.

In step S209, the monitoring server determines a medical server at the shortest distance to the user based on the location information of the user, and transmits help information comprising at least one of the physical sign information, the location information, the first physical symptom information or the second physical symptom information to the medical server. For example, in the environment of FIG. 1, assuming that there are a plurality of medical servers 70, the monitoring server 20 may determine one of the plurality of medical servers 20 which is closest to the user as a medical server to which the help information is transmitted, so as to facilitate medical care workers in a hospital where the medical server is located to quickly reach the location of the user for treatment of the user. The medical care workers using the medical server may determine a health status of the user according to the help information and take corresponding rescue measures.

Figure 4:
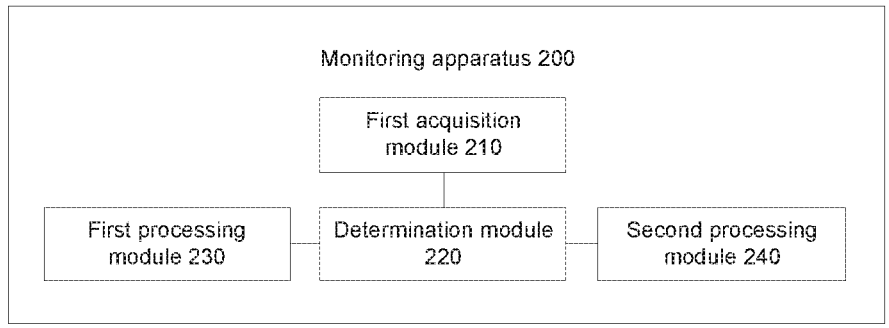
FIG. 4 is a schematic structural diagram of a monitoring apparatus according to an embodiment of the present disclosure.

FIG. 4 is a schematic structural diagram of a monitoring apparatus 200 according to an embodiment of the present disclosure. As shown in FIG. 4, the embodiments of the present disclosure further provide a monitoring apparatus 200. The monitoring apparatus 200 comprises: a first acquisition module 210 configured to acquire physical sign information of a user; a determination module 220 configured to determine whether the physical sign information is in an abnormal state; a first processing module 230 configured to transmit first information based on the physical sign information in a case where the physical sign information is in the abnormal state, so that a first information receiving terminal determines a health status of the user according to the physical sign information and physical symptom information which is acquired by itself based on the first information, wherein the physical symptom information is external manifestation of the user; or a second processing module 240 configured to acquire the physical symptom information of the user in a case where the physical sign information is in the abnormal state, and transmit first information based on the physical sign information and the physical symptom information, so that the first information receiving terminal determines the health status of the user according to the physical sign information and the physical symptom information. For example, the physical sign information of the user acquired by the first acquisition module 210 may comprise various physiological information which may characterize the health status of the user, for example, a heart rate, blood oxygen, a blood pressure etc. The physical symptom information acquired by the second processing module 240 is external manifestation of the user, for example, looks, body movements such as convulsions, vomiting etc. When medial care workers make determination on the health status of the user, the medical care workers may make more accurate determination on the health status of the user based on the physical sign information in combination with the external physical symptom information, and may improve the efficiency of the determination, so as to avoid missing the best time for treatment of the user, thereby improving the efficiency of treatment of the user. In some embodiments, the first information transmitted by the first processing module 230 or the second processing module 240 may further comprise location information, help content, and a preliminary processing result of the physical sign information etc. For example, pre-processing and feature extraction are performed on electrocardiosignal data to obtain a result that an ST segment of the electrocardiosignal physical signal raises, and this result is transmitted to medical care workers to help the medical care workers quickly and accurately determine the health status of the user and take relevant rescue measures in advance, thereby improving the efficiency of treatment.

In some embodiments, the monitoring apparatus 200 further comprises a storage module for storing physical sign information of a healthy person in a normal physiological state. The determination module 220 may make determination on the physical sign information which is acquired currently according to the physical sign information of the healthy person in the normal physiological state which is stored by the storage module. For example, if a normal range of a heart rate of the healthy person stored by the storage module is 60-100 beats/min, and a heart rate which is acquired currently is 120 beats/min, it may be determined by the determination module 220 that the current heart rate is in an abnormal state. In some embodiments, the storage module further stores historical physical sign information of the user, and the determination module 220 makes determination on the physical sign information which is acquired currently using the user's own physical sign information in the normal physiological state which is determined according to stored user's own historical physical sign information. For example, if a normal range of the heart rate of the user in the normal physiological state is determined to be 60-90 beats/min according to the historical physical sign information of the user, and the heart rate which is acquired currently is 95 beats/min, it may be determined by the determination module 220 that the current heart rate of the user is in an abnormal state. In this way, more accurate determination may be made on the health status of the user, which is more personalized.

In some embodiments, the physical symptom information may be obtained from an acquired image or video related to the user, and the image or video related to the user may be acquired by the second processing module 240. For example, in a case where the physical sign information is in an abnormal state, the second processing module 240 transmits a first control command to turn on a camera apparatus on a monitoring device to acquire the physical symptom information of the user. In some embodiments, after receiving the first information transmitted by the first processing module 230 based on the physical sign information, the first information receiving terminal transmits a second control command to a first device which establishes a connection with the monitoring device which acquires the physical sign information. After receiving the second control command, the first device turns on a camera apparatus thereon, acquires physical symptom information of the user using photos or videos taken by the camera apparatus, and transmits the acquired physical symptom information of the user to the first information receiving terminal.

In some embodiments, the first information comprises location information of the user, and after receiving the first information which is transmitted by the first processing module 230 based on the physical sign information, the first information receiving terminal transmits, based on the location information, help information to a second device within a preset range from a location indicated by the location information. After receiving the help information, the second device may ask a user thereof whether to help acquire physical symptom information of the user corresponding to the location information, and after the user confirms to help acquire the physical symptom information of the user, a camera apparatus of the second device is turned on to acquire the physical symptom information of the user, and transmits the physical symptom information to the first information receiving terminal. In some embodiments, after the first information receiving terminal receives the first information which is transmitted by the first processing module 230 based on the physical sign information, the first information receiving terminal transmits the help information to a predetermined server based on the location information. The predetermined server may be a server which is determined based on the location information to be close to the user. In some embodiments, the predetermined server may be a server of a vehicle monitoring system, which receives images and/or videos transmitted by various camera apparatuses for monitoring vehicles, and after receiving the help information, the predetermined server determines camera apparatuses which are close to the location of the user according to the location information, further determines images or videos acquired by the camera apparatuses which may characterize the physical symptom information of the user, and transmits the images or the videos to the first information receiving terminal.

In some embodiments, the first information receiving terminal which receives the first information may be a server of a monitoring center, other devices associated with identification information of the user, etc. The first information receiving terminal may also be a device which is determined according to the location information of the user to be within a certain range from the user. For example, the monitoring apparatus 200 may further comprise a BLE communication module, which transmits the first information to an electronic device within a range of 50 meters from the user in a broadcast manner.

With the monitoring apparatus 200 according to the embodiments of the present disclosure, it may be determined whether the user is currently in an abnormal state according to the physical sign information acquired by the first acquisition module 210, and the first information is transmitted by the first processing module 230 or the second processing module 240 in a case where the user is currently in the abnormal state, wherein the first information may comprise the physical sign information or a combination of the physical sign information and the physical symptom information. When the first information receiving terminal receives the first information, the first information receiving terminal may immediately make a corresponding response, so that the medical care workers may accurately determine the current health status of the user directly or indirectly according to the first information, so as to avoid missing the best time for treatment of the user, thereby improving the efficiency of treatment of the user.

Figure 5:
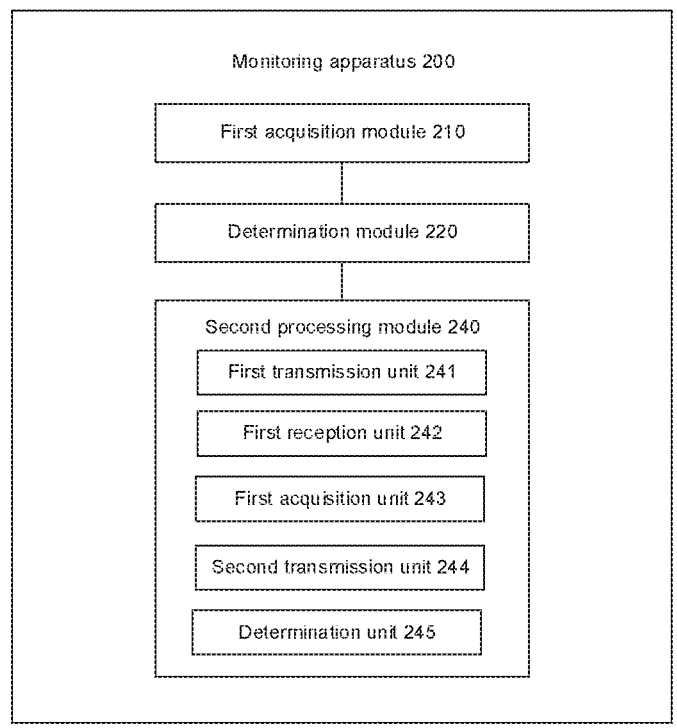
FIG. 5 is a schematic structural diagram of a specific embodiment of a monitoring apparatus according to the present disclosure.

FIG. 5 is a structural diagram of a specific embodiment of the monitoring apparatus 200 according to the embodiment of the present disclosure. As shown in FIG. 5, the second processing module 240 comprises a first transmission unit 241 configured to transmit, to the first device which has established a connection, a second control command for requesting the first device to acquire the physical symptom information; and a first reception unit 242 configured to receive the physical symptom information transmitted by the first device. In some embodiments, the monitoring apparatus 200 further comprises a communication module, and the monitoring apparatus 200 establishes a connection with the first device through the communication module. The first transmission unit 241 transmits the second control command to the first device which has established the connection, so that, after receiving the second control command, the first device turns on a camera apparatus thereon, and uses photos or videos taken by the camera apparatus to acquire the physical symptom information of the user. The first reception unit 242 receives the physical symptom information of the user acquired by the first device, so that the second processing module 240 transmits the first information based on the physical sign information and the physical symptom information. In some embodiments, in order to save power, the monitoring apparatus 200 may establish a connection with the first device in a case where it is determined that the physical sign information is in an abnormal state.

In some embodiments, as shown in FIG. 5, the second processing module 240 comprises: a first acquisition unit 243 configured to acquire location information of the user; and a second transmission unit 244 configured to transmit second information based on the location information to acquire physical symptom information through the second information. In some embodiments, the second transmission unit 244 is specifically configured to transmit the second information to the second device within the preset range from the location indicated by the location information, so that the second device acquires the physical symptom information; and receive the physical symptom information transmitted by the second device. For example, the second information transmitted by the second transmission unit 244 is an operation request for requesting other devices to acquire the physical symptom information of the user, and may carry the location information of the user, help information, and identification information of the monitoring apparatus 200. In some embodiments, the second information may be transmitted by the second transmission unit 244 to the second device within the preset range from the location indicated by the location information. After receiving the second information, the second device may ask a user of the second device whether to help acquire the physical symptom information of the user corresponding to the identification information of the monitoring apparatus 200, and after the user confirms to help acquire the physical symptom information of the user, the camera apparatus on the second device is turned on to acquire the physical symptom information of the user of the monitoring apparatus 200. After acquiring the physical symptom information, the second device transmits the physical symptom information to the second transmission unit 244 of the corresponding monitoring apparatus 200 based on the received identification information of the monitoring apparatus 200, so that the second processing module 240 transmits the first information based on the physical sign information and the physical symptom information to improve the efficiency of treatment of the user.

In some embodiments, the second transmission unit 244 is specifically configured to transmit the second information to the predetermined server to cause the predetermined server to acquire physical symptom information collected by a third device based on the second information; and receive the physical symptom information transmitted by the predetermined server, wherein the second information carries the location information. For example, the predetermined server may be a server which is determined based on the location information to be close to the user. In some embodiments, the predetermined server may be a server of the vehicle monitoring system, which receives images and/or videos transmitted by various camera apparatuses for monitoring vehicles. In a case where the physical sign information is in an abnormal state, the second information may be transmitted by the second processing module 240 to the predetermined server based on the location information of the user which acquired by the first acquisition unit 243, so that, after receiving the second information, the predetermined server determines camera apparatuses which are close to the location of the user according to the location information, further determines images or videos acquired by the camera apparatuses which may characterize the physical symptom information of the user, and transmits the determined images or videos to the monitoring apparatus 200. The second processing module 240 receives the images or the videos transmitted by the predetermined server, and process the images or the videos to obtain the physical symptom information. The predetermined server may also be other servers, for example, a corresponding image collection server in a road network.

In some embodiments, the second processing module 240 further comprises a determination unit 245 configured to determine a medical server (hereinafter also referred to as a fourth device) at the shortest distance to the user based on the location information; and transmit the first information to the fourth device. For example, the fourth device may be various kinds of devices which are determined based on the location information to be at the shortest distance to the user, for example, a server of a monitoring center, a server of a hospital information system, an electronic device which has established a connection with the device which transmits the first information, etc. The first information is transmitted by the determination unit 245 to the fourth device at the shortest distance to the user, so that a user of the fourth device may rush to the site to treat the user as soon as possible after receiving the first information, thereby improving the efficiency of the treatment of the user.

In some embodiments, as shown in FIG. 5, the first processing module 230 or the second processing module 240 may further be configured to analyze a cause of occurrence of the abnormal state based on the physical sign information and medical record information of the user; and generate and transmit first information based on an analysis result. For example, the first processing module 230 or the second processing module 240 determines whether the user satisfies characteristics of a disease recorded in the medical record information of the user based on the physical sign information and/or a preliminary processing result of the physical sign information; and generates and transmits the first information based on an analysis result, so that the medical care workers may quickly and accurately determine the current health status of the user according to the analysis result in combination with the physical sign information and the physical symptom information, thereby improving the efficiency of the treatment of the user.

In some embodiments, the above modules may be integrated on the same device, or may be selectively combined and integrated on different devices, for example, the first acquisition module 210, the determination module 220, and the second processing module 240 are integrated on the same monitoring device, and the first processing module 230 is integrated on another device communicatively coupled to the monitoring device.

Figure 6:
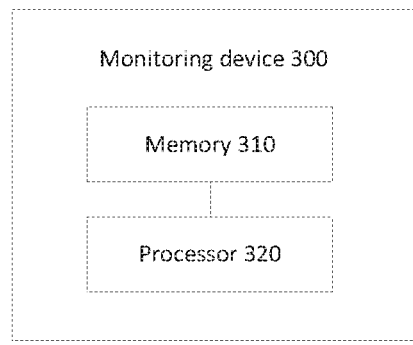
FIG. 6 is a schematic structural diagram of a monitoring device according to an embodiment of the present disclosure.

FIG. 6 is a schematic structural diagram of a monitoring device 300 according to an embodiment of the present disclosure. As shown in FIG. 6, the embodiments of the present disclosure further provide a monitoring device 300. The monitoring device 300 comprises a memory 310 and a processor 320, wherein the memory 310 has stored thereon computer executable instructions which, when executed by the processor 320, implement the monitoring method according to any of the embodiments of the present disclosure.

In some embodiments, the monitoring device 300 further comprises a monitoring unit configured to acquire physical sign information of a user and a camera apparatus configured to acquire physical symptom information. The monitoring unit may comprise an electrocardiosignal monitoring unit, a blood oxygen signal monitoring unit, etc., which is not specifically limited here. After acquiring the physical sign information, the processor 320 determines whether the physical sign information is in an abnormal state; transmits a control command to the camera apparatus to acquire the physical symptom information of the user in a case where it is determined that the physical sign information is in the abnormal state; and then transmits first information based on the physical sign information and the physical symptom information, so that medical care workers quickly provide a determination result of a current health status of the user based on the first information and take relevant rescue measures in advance, thereby improving the efficiency of treatment. In some embodiments, the monitoring device 300 further comprises a storage unit for storing physical sign information of a healthy person in a normal physiological state. The processor 320 may make determination on the physical sign information which is acquired currently according to the stored physical sign information of the healthy person in the normal physiological state. For example, if a normal range of a heart rate of the healthy person stored by the storage module is 60-100 beats/min, and a heart rate which is acquired currently is 120 beats/min, it may be determined by the processor 320 that the current heart rate is in an abnormal state. In some embodiments, the storage unit further stores historical physical sign information of the user, and the processor 320 processes historical physical sign information of the user to obtain physical sign information of the user in a normal state, and makes determination on the current physical sign information according to the physical sign information of the user in the normal state. For example, if a normal range of the heart rate of the user is determined to be 60-90 beats/min according to the historical physical sign information of the user, and the heart rate which is acquired currently is 95 beats/min, it may be determined by the processor 320 that the current heart rate of the user is in an abnormal state. In this way, more accurate determination may be made on the health status of the user, which is more personalized.

In some embodiments, the monitoring device 300 further comprises a location acquisition unit and a communication unit. The location acquisition unit is configured to acquire current location information of the user, and the communication unit is configured to establish communication between the monitoring device 300 and other devices, wherein the physical symptom information of the user which is acquired by the processor 320 may come from the other devices which communicate with the monitoring device 300. In some embodiments, the physical symptom information of the user comes from an electronic device which establishes a connection with the monitoring device 300 through the communication unit, for example, a smart phone. After receiving second information transmitted by the monitoring device 300 for acquiring the physical symptom information, the smart phone turns on a camera apparatus thereon to acquire images and/or videos which may characterize the physical symptom information of the user and transmits the physical symptom information to the monitoring device 300. In some embodiments, the physical symptom information of the user comes from an electronic device which is determined based on the location information to be within a preset range from the current location of the user. Specifically, the communication unit may transmit the second information to the electronic device within the preset range in a broadcast manner, and after receiving the second information, the electronic device within the preset range may ask a user thereof whether to help acquire physical symptom information of the user corresponding to the identification information of the monitoring device 300, and after the user confirms to help acquire the physical symptom information of the user, a camera apparatus of the electronic device is turned on to acquire the physical symptom information of the user of the monitoring device 300, and after acquiring the physical symptom information, transmits the physical symptom information to the corresponding monitoring device 300 based on the received identification information of the monitoring device 300. In some embodiments, the monitoring device 300 may transmit the second information to a predetermined server, and the predetermined server may be a server of a vehicle monitoring system, which receives images and/or videos transmitted by various camera apparatuses for monitoring vehicles, and after receiving the second information, the predetermined server determines camera apparatuses which are close to the location of the user according to the location information, further determines images or videos acquired by the camera apparatuses which may characterize the physical symptom information of the user, and transmits the determined images or the videos to the monitoring device 300.

In some embodiments, the processor 320 may further determine a device at the shortest distance to the user based on the location information, and transmit the first information to the device, so that a user of the device rushes to the site to treat the user as soon as possible after receiving the first information, thereby improving the efficiency of the treatment of the user.

In some embodiments, the processor 320 may, in a case where the physical sign information is in the abnormal state, analyze a cause of occurrence of the abnormal state based on the physical sign information and medical record information of the user, for example, determine whether the user satisfies characteristics of a disease recorded in the medical record information of the user based on the physical sign information and/or a preliminary processing result of the physical sign information; and generate and transmit the first information based on an analysis result, so that the medical care workers may quickly and accurately determine the current health status of the user according to the analysis result in combination with the physical sign information and the physical symptom information, thereby improving the efficiency of the treatment of the user.

With the monitoring device 300 according to the embodiments of the present disclosure, it may be determined whether the user is currently in an abnormal state according to the acquired physical sign information, and the first information is transmitted in a case where the user is currently in the abnormal state, wherein the first information may comprise the physical sign information or a combination of the physical sign information and the physical symptom information. When the first information receiving terminal receives the first information, the first information receiving terminal may immediately make a corresponding response, so that the medical care workers may accurately determine the current health status of the user directly or indirectly according to the first information, so as to avoid missing the best time for treatment of the user, thereby improving the efficiency of treatment of the user.

Figure 7:
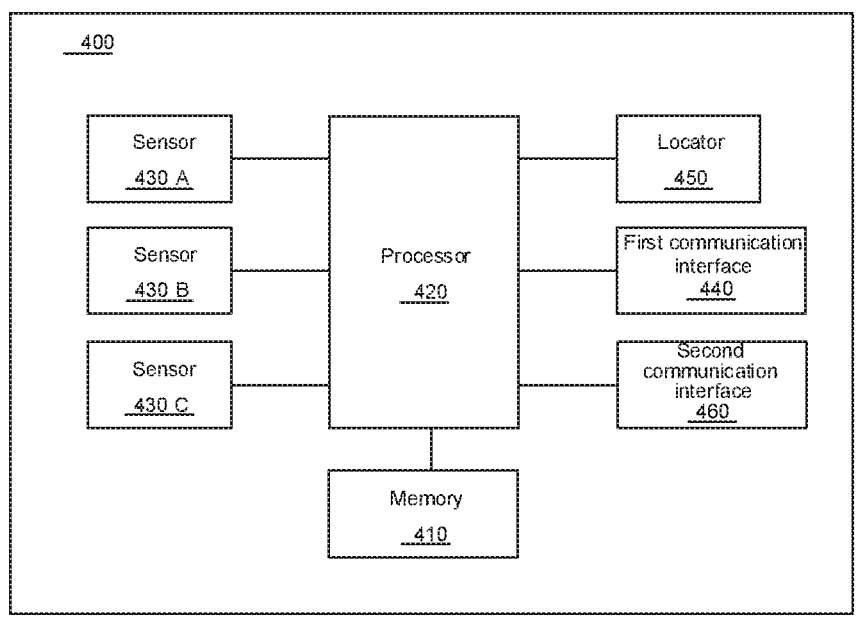
FIG. 7 is a schematic structural diagram of a monitoring device according to another embodiment of the present disclosure.

FIG. 7 illustrates a schematic block diagram of a monitoring device according to another embodiment of the present disclosure. As shown in FIG. 7, the monitoring device 400 comprises a memory 410 and a processor 420. The memory 410 has stored therein instructions which, when executed by the processor 420, cause the processor 420 to execute the monitoring method according to any of the above embodiments. As shown in FIG. 7, the monitoring device 400 may further comprise a plurality of sensors 430A, 430B, and 430C coupled to the processor 420, which are used to collect various physical sign information of a user respectively and provide the physical sign information to the processor. For example, the sensor 430A is used to sense a blood pressure of the user, the sensor 430B is used to sense a heart rate of the user, and so on.

The monitoring device 400 may further comprise a first communication interface 440 coupled to the processor 420, and the processor 420 may communicate with the above first electronic device through the first communication interface 440. The first communication interface 440 may be a short-range communication interface, for example, a Bluetooth communication interface.

The monitoring device 400 may further comprise a locator 450 coupled to the processor 420, for example, a GPS locator. The locator 450 may acquire location information of the user and provide the location information to the processor 420.

The monitoring device 400 may further comprise a second communication interface 460 coupled to the processor 420, and the processor 420 may communicate with the above monitoring server through the second communication interface 460. The second communication interface 460 is, for example, but not limited to, a wired communication interface or a wireless communication interface.

Figure 8:
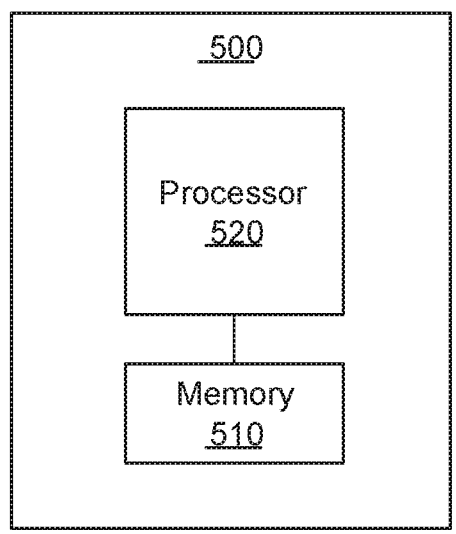
FIG. 8 is a schematic structural diagram of a monitoring server according to an embodiment of the present disclosure.

FIG. 8 illustrates a schematic block diagram of a monitoring server according to another embodiment of the present disclosure. As shown in FIG. 7, the monitoring server 500 comprises a memory 510 and a processor 520. The memory 510 has stored therein instructions which, when executed by the processor 520, cause the processor 520 to perform the monitoring method according to any of the above embodiments.

The above description is intended to be illustrative and not restrictive. For example, the above examples (or one or more solutions thereof) may be used in combination with each other. For example, those of ordinary skill in the art may use other embodiments when reading the above description. In addition, in the above specific implementations, various features may be grouped together to simplify the present disclosure. This should not be interpreted as an intent that an unclaimed feature disclosed is necessary for any claim. Rather, the subject matters of the present disclosure may be less than all features of certain embodiments disclosed. Accordingly, the following claims are hereby incorporated into the detailed implementations as examples or embodiments, wherein each claim is independently regarded as a separate embodiment, and it is considered that these embodiments may be combined with each other in various combinations or arrangements. The scope of the present disclosure should be determined with reference to the full scope of the appended claims and equivalents to which these claims are entitled.

The above embodiments are only exemplary embodiments of the present disclosure, and are not used to limit the present disclosure, and the protection scope of the present disclosure is defined by the claims. Those skilled in the art may make various modifications or equivalent replacements to the present disclosure within the essence and protection scope of the present disclosure, and such modifications or equivalent replacements shall also be deemed to fall within the protection scope of the present disclosure.

We claim:

1. A monitoring method, comprising:
    acquiring physical sign information of a user;
    determining whether a physical sign of the user is in an abnormal state based on the physical sign information;
    acquiring first physical symptom information of the user in response to the physical sign of the user being in the abnormal state; and
    transmitting the physical sign information and the first physical symptom information to a monitoring server to determine a health status of the user,
    wherein acquiring first physical symptom information of the user comprises:
    transmitting, to a first electronic device with which a short-range communication connection has been established based on a short-range communication protocol, a first request for requesting the first electronic device to acquire the first physical symptom information of the user; and
    receiving the first physical symptom information transmitted by the first electronic device.

2. The monitoring method according to claim 1, further comprising:
    acquiring location information of the user; and
    transmitting the location information to the monitoring server, so that the monitoring server acquires second physical symptom information of the user based on the location information.

3. The monitoring method according to claim 2, wherein acquiring second physical symptom information of the user based on the location information comprises:
    transmitting, to a second electronic device within a first preset range from the user based on the location information, a second request for requesting the second electronic device to acquire the second physical symptom information of the user; and
    receiving the second physical symptom information transmitted by the second electronic device.

4. The monitoring method according to claim 2, wherein acquiring second physical symptom information of the user based on the location information comprises:
    transmitting, to a traffic server, a third request comprising the location information for requesting the traffic server to control a traffic image collector within a second preset range from the user to acquire the second physical symptom information of the user; and
    receiving the second physical symptom information transmitted by the traffic server.

5. The monitoring method according to claim 4, wherein the traffic image collector comprises at least one of a camera installed on a street or a driving recorder installed on a vehicle.

6. The monitoring method according to claim 2, further comprising:
    determining, by the monitoring server, a medical server at the shortest distance from the user based on the location information; and
    transmitting, by the monitoring server, help information comprising at least one of the physical sign information, the location information, the first physical symptom information, or the second physical symptom information to the medical server.

7. The monitoring method according to claim 1, further comprising:
    acquiring medical record information of the user in response to the physical sign of the user being in the abnormal state;
    analyzing a cause of occurrence of the abnormal state based on the physical sign information and the medical record information of the user; and
    transmitting an analysis result to the monitoring server.

8. The monitoring method according to claim 1, wherein the physical sign information comprises at least one of a blood pressure, a blood glucose, a blood oxygen content, a heart rate, or a pulse.

9. A monitoring device, comprising:
    a memory having stored therein instructions; and
    a processor configured to execute the instructions to:
    acquire physical sign information of a user;
    determine whether a physical sign of the user is in an abnormal state based on the physical sign information;
    acquire first physical symptom information of the user in response to the physical sign of the user being in the abnormal state; and
    transmit the physical sign information and the first physical symptom information to a monitoring server to determine a health status of the user,
    wherein the processor is further configured to transmit, to a first electronic device with which a short-range communication connection has been established based on a short-range communication protocol, a first request for requesting the first electronic device to acquire the physical symptom information of the user, and receive the physical symptom information transmitted by the first electronic device.

10. The monitoring device according to claim 9, further comprising:
  a plurality of sensors coupled to the processor, and configured to collect the physical sign information of the user and provide the physical sign information to the processor.

11. The monitoring device according to claim 9, further comprising a first communication interface through which the processor communicates with the first electronic device.

12. The monitoring device according to claim 9, further comprising:
  a locator coupled to the processor, and configured to acquire location information of the user and provide the location information to the processor,
  wherein the processor is further configured to transmit the location information to the monitoring server, so that the monitoring server acquires physical symptom information of the user based on the location information.

13. The monitoring device according to claim 9, wherein the processor is further configured to:
  acquire medical record information of the user in response to the physical sign of the user being in the abnormal state;
  analyze a cause of occurrence of the abnormal state based on the physical sign information and the medical record information of the user; and
  transmit an analysis result to the monitoring server.

14. The monitoring device according to claim 9, further comprising a second communication interface through which the processor communicates with the monitoring server.

15. A monitoring server comprising a memory and a processor, wherein the memory has stored therein instructions, and the processor is configured to execute the instructions to:
  receive physical sign information and first physical symptom information of a user from a monitoring device, wherein the first physical symptom information is acquired by the monitoring device in response to a physical sign of the user being in an abnormal state; and
  determine a health status of the user according to the physical sign information and the first physical symptom information,
  wherein the processor is further configured to:
  receive location information of the user from the monitoring device;
  transmit, to a second electronic device within a first preset range from the user, a second request for requesting the second electronic device to acquire second physical symptom information of the user; and
  receive the second physical symptom information transmitted by the second electronic device.

16. The monitoring server according to claim 15, wherein the processor is further configured to:
  transmit, to a traffic server, a third request comprising the location information for requesting the traffic server to control a traffic image collector within a second preset range from the user to collect the second physical symptom information of the user based on the location information; and
  receive the second physical symptom information transmitted by the traffic server.

17. The monitoring server according to claim 15, wherein the processor is further configured to:
  determine a medical server at the shortest distance from the user based on the location information; and
  transmit help information comprising at least one of the physical sign information, the location information, the first physical symptom information, or the second physical symptom information to the medical server.

* * * * *